(12) United States Patent
Pan et al.

(10) Patent No.: US 9,594,053 B2
(45) Date of Patent: Mar. 14, 2017

(54) SYSTEM AND METHOD FOR FLAT PANEL DETECTOR GEL AND BLOT IMAGING

(71) Applicant: General Electric Company, Schenectady, NY (US)

(72) Inventors: Feng Pan, Clifton Park, NY (US); Brian David Yanoff, Niskayuna, NY (US); Aaron Judy Couture, Schenectady, NY (US); Hakan Erik Roos, Uppsala (SE); Yu Zhao, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 378 days.

(21) Appl. No.: 14/264,133

(22) Filed: Apr. 29, 2014

(65) Prior Publication Data

US 2015/0285761 A1 Oct. 8, 2015

Related U.S. Application Data

(63) Continuation of application No. 14/245,041, filed on Apr. 4, 2014.

(51) Int. Cl.
*G01N 27/447* (2006.01)

(52) U.S. Cl.
CPC . *G01N 27/44726* (2013.01); *G01N 27/44721* (2013.01)

(58) Field of Classification Search
CPC .................................................. G01N 27/447
See application file for complete search history.

(56) References Cited

U.S. PATENT DOCUMENTS

| | | | |
|---|---|---|---|
| 6,800,438 B2 | 10/2004 | Noolandi et al. | |
| 2003/0157581 A1 | 8/2003 | Grill et al. | |

(Continued)

FOREIGN PATENT DOCUMENTS

| | | |
|---|---|---|
| GB | 2374924 A | 10/2002 |
| JP | 5172614 B2 | 5/2010 |

(Continued)

OTHER PUBLICATIONS

Esposito et al., "Using a large area CMOS APS for direct chemiluminescence detection in Western Blotting Electrophoresis," SPIE Medical Imaging Conference, San Diego, CA, Feb. 2012, pp. 1-8.

(Continued)

*Primary Examiner* — Jennifer Dieterle

(57) ABSTRACT

A system and method for generating a digital image in fluorescence gel imaging is disclosed. The method includes providing a gel sample and placing the gel sample on a flat panel detector having array of photodiodes and transistors that collect light generated from the gel sample. The gel sample is illuminated using a light source integrated into the flat panel imaging system and light emitted by the gel sample responsive to an excitation of the gel sample by light provided by the light source is then collected, with the light emitted by the gel sample being collected by the array of photodiodes of the flat panel detector and converted to electric charges to generate light data. The light data is then processed to generate a digital image of the gel sample.

19 Claims, 12 Drawing Sheets

(56) References Cited

U.S. PATENT DOCUMENTS

| | | | |
|---|---|---|---|
| 2005/0109951 A1* | 5/2005 | Fish | G01N 21/64 |
| | | | 250/461.1 |
| 2006/0051816 A1 | 3/2006 | Hsieh et al. | |
| 2007/0252953 A1* | 11/2007 | Metzger | G02B 27/2228 |
| | | | 353/7 |
| 2008/0081769 A1 | 4/2008 | Hassibi | |
| 2009/0121982 A1* | 5/2009 | Choi | H01L 27/3262 |
| | | | 345/76 |
| 2013/0143209 A1* | 6/2013 | Strong | G01N 21/07 |
| | | | 435/6.11 |
| 2013/0157282 A1 | 6/2013 | Bouzid et al. | |
| 2013/0177930 A1 | 7/2013 | Zhang | |
| 2013/0199930 A1* | 8/2013 | Tamari | G01N 27/44704 |
| | | | 204/461 |
| 2014/0106989 A1 | 4/2014 | Barich et al. | |
| 2014/0158541 A1* | 6/2014 | Beaudet | G01N 27/44726 |
| | | | 204/612 |

FOREIGN PATENT DOCUMENTS

| | | | |
|---|---|---|---|
| JP | 2010117167 | * | 5/2010 |
| WO | 99/14358 A1 | | 3/1999 |
| WO | 2015/017046 A1 | | 2/2015 |

OTHER PUBLICATIONS

International Search Report and Written Opinion regarding Intenrational Application No. PCT/EP2015/071233, mail date Jul. 20, 2016, 18 pages.

* cited by examiner

SYSTEM AND METHOD FOR FLAT PANEL DETECTOR GEL AND BLOT IMAGING

CROSS-REFERENCE TO RELATED APPLICATION

The present application is a continuation of, and claims priority to, U.S. patent application Ser. No. 14/245,041, filed Apr. 4, 2014, the disclosure of which is incorporated herein by reference.

BACKGROUND OF THE INVENTION

Embodiments of the invention relate generally to gel and blot imaging and, more particularly, to a system and method for performing gel and blot imaging using a flat panel imaging system.

Gel electrophoresis and electroblotting are commonly used techniques for the separation and analysis of macromolecules (DNA, RNA and proteins) and the subsequent transfer of such macromolecules onto a membrane, respectively, that then enables further analysis of these macromolecules using probes, such as specific antibodies, ligands, or stains, that can and/or drive a reaction and produce a color blot (e.g., Western blot imaging and Southern blot imaging). Several detection techniques may be employed in gel and blot imaging for DNA and/or protein analysis, including the detection, recognition, and quantification of specific macromolecules in a sample of tissue homogenate or extract. Such techniques include fluorescent detection, chemiluminescent detection, and colorimetric detection. In fluorescent detection, a fluorescently labeled stain or probe is excited by light and the emission of the excitation is then detected by a photosensor (e.g., a charge coupled device (CCD) camera) that captures a digital image of the gel/blot and allows further data analysis, such as molecular weight analysis and a quantitative western blot analysis. In chemiluminescent detection, a blot is incubated with a substrate that will luminesce when exposed to a reporter on the antibody—with the light that is generated being detected by photographic film to create an image of the blot thereon or by CCD cameras to capture a digital image of the blot.

The performing of fluorescent detection, chemiluminescent detection, and/or colorimetric detection according to existing techniques—specifically with respect to the use of film emulsion and/or CCD cameras to capture images—presents some drawbacks and limitations. For example, film emulsion is the conventional detection medium for chemiluminescent detection, but is characterized by non-linear response and limited dynamic range requiring multiple exposures, thereby resulting in a time-consuming and expensive imaging procedure. As another example, as chemiluminescent signals generated from the blots are normally weak and time-varying, relatively fast exposure (e.g., on the order of a minute), low noise, and high light detection efficiency is required for accurate image capture when using CCDs. Thus, limitations of the CCDs regarding operation at a low frame rate (due to the inherent sequential read-out thereof) and low temperature (to achieve a reasonable noise level) present challenges in accurately capturing the chemiluminescent signals. Still further, CCDs require a high efficiency optical lens to focus the large blot to small CCD chips (~1 cm$^2$)—with the optical lens adding to the cost of the high-end CCDs, increasing the size and vertical space of the imaging device (due to the large working distance of the CCD camera), and also causing problems with regard to light collection efficiency (due to the large working distance). Yet still another drawback of image capture via CCD is that the capturing of images can take approximately 3-20 minutes—depending on the desired exposure.

Other more recent attempts to provide a system that captures a digital image of the blot include a C-digit system released by LICOR Biosciences that utilizes a linear scanner with sixteen linear sensors. The linear scanner combines short working distance (like film emulsion) to maximize light collection efficiency and multiple small low cost linear sensor arrays to meet the data acquisition time requirement, but the scan time to scan the large area is still around multiple minutes per pass (i.e., 6-12 minutes). Additionally, there is a concern that during the scanning time (on order of 10 minutes), the transient behavior of the chemiluminescence in the blot itself will be changing. As such—as the linear scan is happening—the intensity at the beginning of the scan will be higher than the intensity of at the end of the scan (bottom of the scan), therefore introducing an artificial gradient in the measurement.

Therefore, it would be desirable to provide a system and method for image acquisition in gel and blot imaging that overcomes the aforementioned drawbacks of conventional imaging techniques and associated systems. It would also be desirable for such systems and methods to provide improved performance in regards to sensitivity, dynamic range, exposure time, and quantum efficiency, while eliminating costly high-efficiency imaging optics such as are used with existing CCD image sensors, so as to provide a system at a reduced cost and size.

BRIEF DESCRIPTION OF THE INVENTION

In accordance with one aspect of the invention, a method for generating a digital image in fluorescence detection gel imaging includes providing a gel sample having a gel and a sample of macromolecules therein and placing the gel sample on a flat panel detector of a flat panel imaging system, the flat panel detector comprising an array of photodiodes and transistors that collect light generated from the gel sample. The method also includes illuminating the gel sample using a light source integrated into the flat panel imaging system and collecting light emitted by the gel sample responsive to an excitation of the gel sample by light provided by the light source, with the light emitted by the gel sample being collected by the array of photodiodes of the flat panel detector and converted to electric charges to generate light data. The method further includes processing the light data to generate a digital image of the gel sample, the processing and image generation being performed by an image reconstructor separate from or incorporated into the flat panel imaging system.

In accordance with another aspect of the invention, a method of generating a digital image in fluorescence detection gel imaging includes providing a gel sample labeled with a fluorescent reagent, the gel sample having macromolecules labeled by the fluorescent reagent. The method also includes positioning the gel sample within a flat panel imaging system to provide for capturing of a digital image of the gel sample, the positioning of the gel sample within the flat panel imaging system further including placing the gel sample on a flat panel matrix-based light sensor comprising an array of photodiodes and transistors and closing a lid of the flat panel imaging system to create a closed environment for capturing of the digital image. The method further includes illuminating the gel sample using a light source integrated into the lid of the flat panel imaging system so as to excite the fluorescent reagent causing the gel sample to generate fluorescent light and detecting the fluorescent light emitted by the gel sample using the flat panel matrix-based light sensor, with the fluorescent light being collected by the array of photodiodes, converted to electric charges, and subsequently converted to digital signals. The method still further includes providing the digital signals to an image reconstructor to process the digital signals and generate a digital image of the gel sample.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Embodiments of the invention relate generally to gel and blot imaging and, more particularly, to a system and method for performing gel and blot imaging using a flat panel imaging system. The flat panel imaging system is a two-dimensional light sensitive image detector array which provides a digital image of the light collected on the detector surface. According to embodiments of the invention, the flat panel imaging system may be specifically constructed to function under chemiluminescence, absorbance (colorimetric), and fluorescence gel and blot imaging modes.

Figure 1:
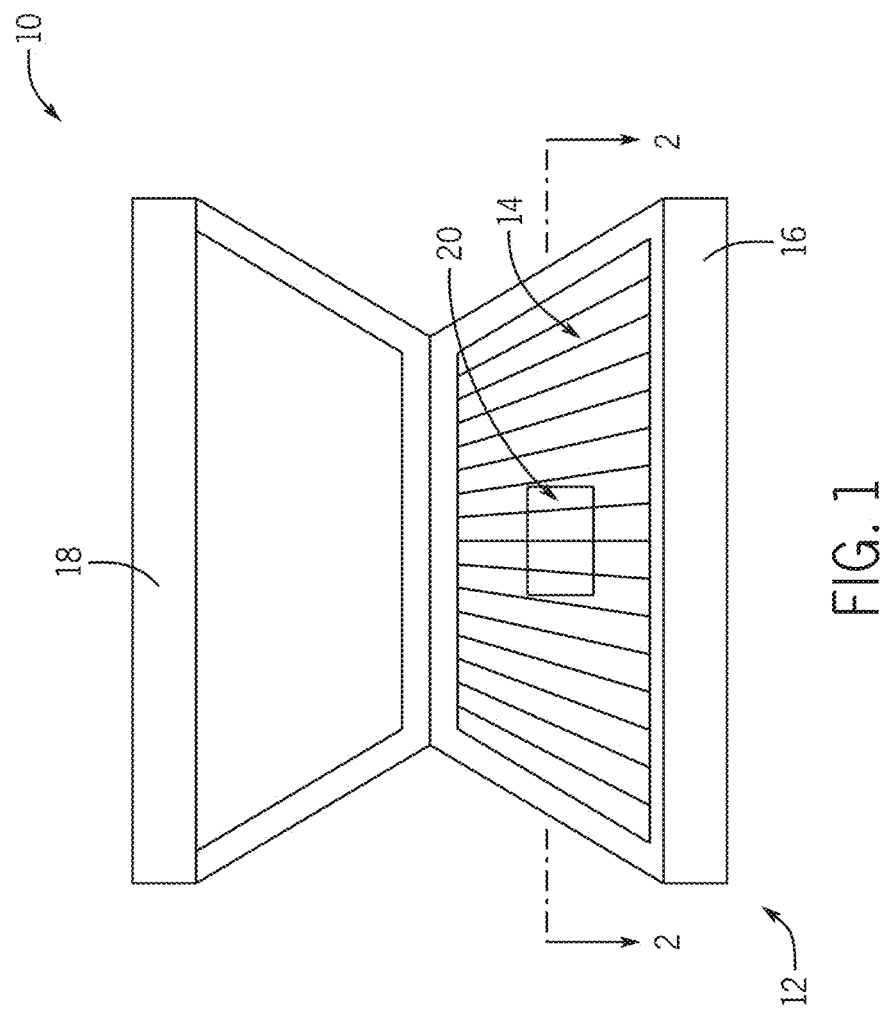
FIG. 1 is an elevated perspective view of a flat panel imaging system, including a flat panel detector, according to an embodiment of the invention.

Referring to FIGS. 1-4, a flat panel imaging system 10 for use in a gel and blot digital image acquisition is provided according to an embodiment of the invention. FIG. 1 provides an elevated perspective view of the flat panel imaging system 10 generally including an outer housing 12 that houses a flat panel detector 14 therein to surround and protect the physical light receptors, electronic detection equipment and associated electronics of the flat panel detector 14. The outer housing 12 includes a base portion 16 that encases the flat panel detector 14 and a lid 18 that, according to one embodiment, is hinged to the base portion 16 so as to be selectively opened and closed with respect to the base portion to provide a "closed environment" to exclude external sources of light for performing of a gel/blot image acquisition.

The flat panel detector 14 of the flat panel imaging system 10 functions as the light detection device in the gel or blot image acquisition. In performing the image acquisition, a "gel sample" or "blot sample" 20 is placed directly onto the imaging surface of the flat panel detector 14, such that photons generated during the image acquisition are directly and efficiently collected from the gel/blot sample. The "gel sample" is understood to refer to an agarose/polyacrylamide gel alone (with protein/DNA/RNA sample therein), while the "blot sample" is understood to refer to an macromolecules (i.e., protein/DNA/RNA sample therein) transferred from the gel onto a membrane. The flat panel detector 14 provides a digital image of the light collected on the detector surface, with the digital image being a quasi-stationary image with desirable signal-to-noise ratio.

Figure 2:
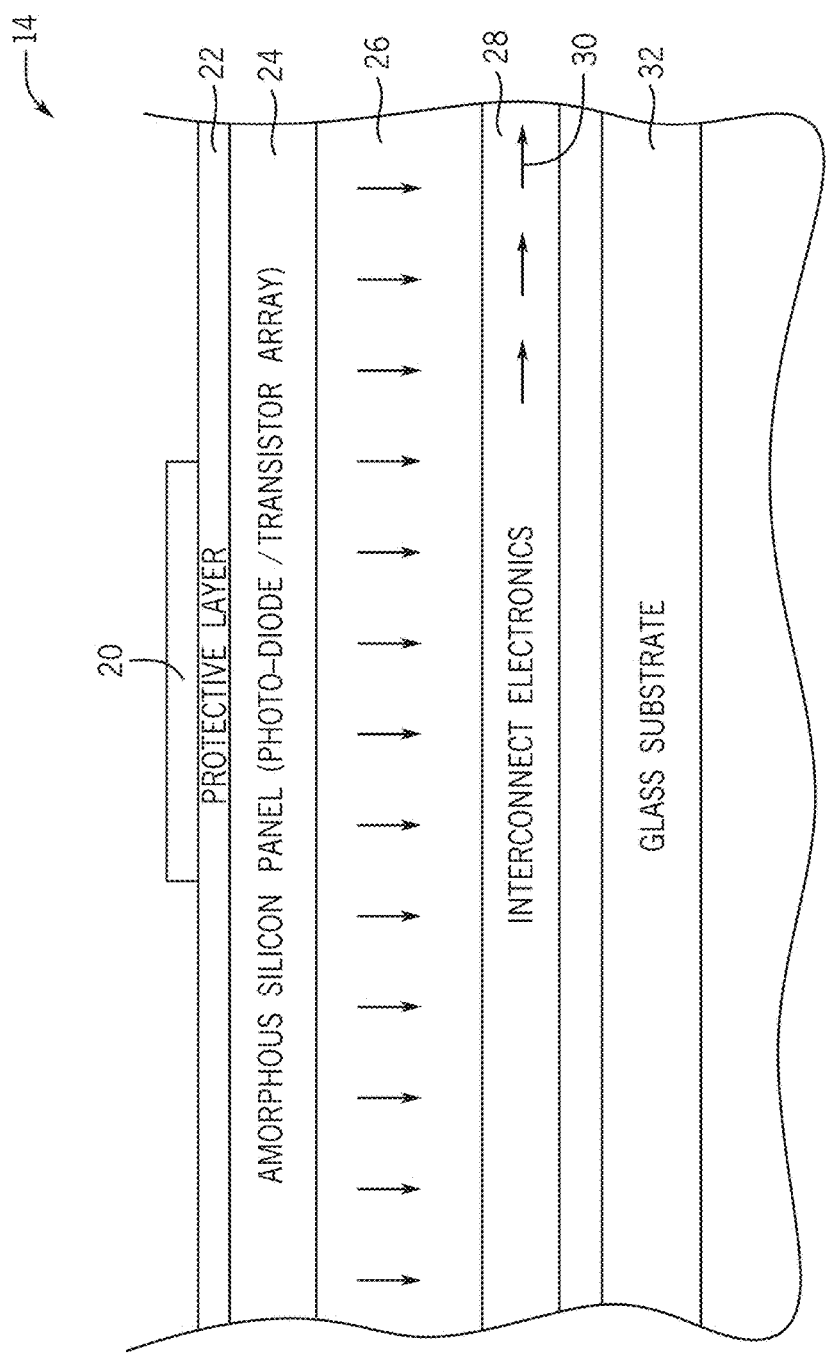
FIG. 2 is an exploded sectional view of the flat panel detector of FIG. 1 taken along line II-II, according to an embodiment of the invention.

Referring now to FIG. 2, an exploded sectional view of the flat panel detector 14 taken along line II-II of FIG. 1 is provided to better illustrate a construction of the flat panel detector. As shown, the flat panel detector 14 includes a top protective layer 22 that provides protection to the components of the detector and that also receives the gel or blot directly thereon. Photons generated during the gel/blot image acquisition pass through protective layer 22 and are absorbed by an array of photodetectors (i.e., photodiode/transistor array) that, according to an exemplary embodiment, is formed from amorphous silicon panel 24. While the array of photodetectors is described hereafter as being formed of an amorphous silicon 24, it is recognized that poly-silicon, an organic photodiode, or crystal silicon technology could instead be employed. As an example, in an embodiment where an organic photodiode is employed, the organic photodiode material may include an electron blocking layer including aromatic tertiary amines and polymeric aromatic tertiary amines, a mixture of a donor material containing a low bandgap polymer, and an acceptor material containing a fullerene material.

The photodiode/transistor array of the amorphous silicon panel 24 receives and converts photons into a plurality of representative image data values 26. Image data values 26 are received in analog form by interconnect electronics 28 and output therefrom as analog image data 30. Amorphous silicon panel 24 and interconnect electronics 28 are formed on silicon glass substrate 32 through semiconductor technology known in the art. For example, in fabrication, eleven layers of amorphous silicon, various metals, and insulators are deposited by plasma enhanced chemical vapor deposition ("PECVD"), sputtering and meniscus coating to form field effect transistors ("FETs"), diodes, interconnects, and contacts. Together, the protective layer 22, amorphous silicon panel 24, interconnect electronics 28, and glass substrate 32 form a flat panel detector 14.

With respect to the top protective layer 22, the layer is constructed to specifically accommodate placement of a gel or blot 20 thereon and provide for accurate photon capture of the gel/blot. The protective layer 22 is thus formed so as to be transparent, sufficiently hard so as to resist scratching, and chemically resistant so as to allow wipe-down thereof with cleaning solvents after removal of a gel/blot upon completion of a digital image acquisition. According to embodiments of the invention, the protective layer 22 may be constructed of glass, mylar, or another suitable thin, tough plastic, or may be a combination of both glass and plastic, where the plastic top sheet is a replaceable layer. It is also recognized that, rather than a replaceable layer being included on protective layer 22, a removable protective layer or protective sleeve could be utilized to protect/enclose the blot sample (i.e., the membrane on which the sample is provided). In each embodiment, the surfaces of protective layer 22 can also be coated with a conductive polymer (PDOT) or indium tin oxide (ITO), for example, so as to prevent artifacts or damage that might occur if statically charged samples (e.g., saran wrap) are placed on the detector.

According to an exemplary embodiment, the protective layer 22 is constructed as a "thin" layer having a thickness of ~25-75 um (e.g., 50 um) in order to prevent light spreading and maintain good spatial resolution, with the protective layer 22 providing for optimal transmission of photons therethrough so as not to degrade the modulation transfer function (MTF) of the amorphous silicon panel 24. The protective layer 22 also provides thermal isolation between the gel/blot 20 and the amorphous silicon panel 24, which is desirable as it is recognized that the placement of cold liquid gels/blots in contact with the imager—coupled with the long acquisition times (on the order of minutes) that might be present in, for example, western blot imaging—can cause local changes in temperature, which in turn affect the leakage current in the photodiodes, which can cause image artifacts. Additionally, the protective layer 22 may incorporate an angle discriminating film thereon to increase contrast and decrease crosstalk of light received by the flat panel detector 14.

As can be seen in FIG. 2, the flat panel detector 14 does not include a scintillator material therein that is often found in such detectors—such as in flat panel detectors used for various x-ray imaging applications. As the detector 14 acquires photons/light emissions directly from a gel or blot sample via use of the photodiodes, no scintillator is required for converting x-ray/radiation into photons prior to receiving of the photons by the photodiodes. Accordingly, the flat panel detector 14 is specifically constructed for use in capturing digital images of macromolecules (e.g., proteins, DNA, RNA) that are analyzing via gel and blot imaging, microtiter plate imaging, etc.

Figure 3:
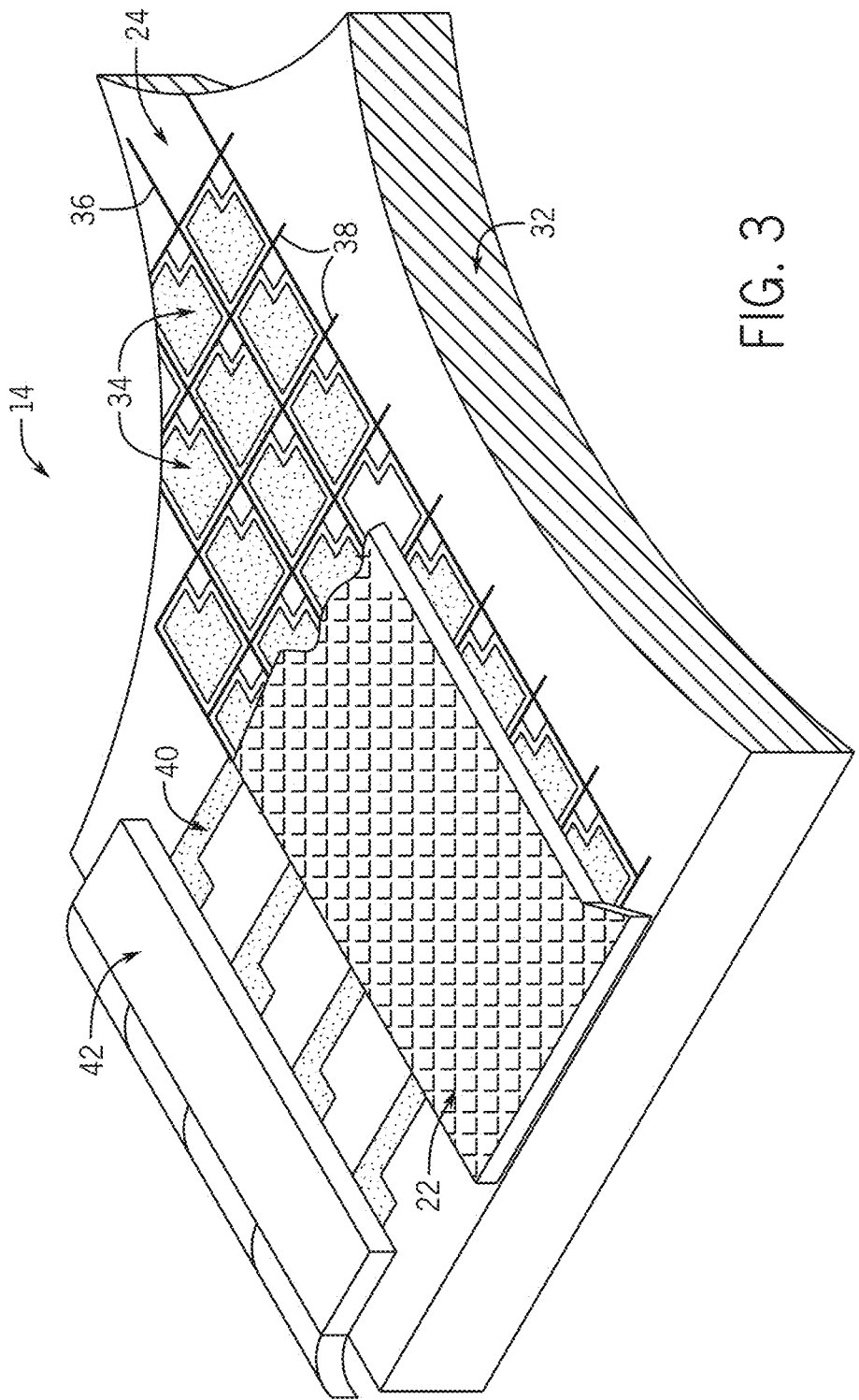
FIG. 3 is an elevated prospective view of the flat panel detector of FIG. 1 removed from a protective base portion, according to an embodiment of the invention.

Referring now to FIG. 3, an elevated prospective view of the flat panel detector 14 removed from base portion 16 (FIG. 1) is provided. As illustrated in FIG. 3, the top protective layer 22 covers the amorphous silicon panel 24, with the amorphous silicon panel being comprised of an array of photo cells or pixels 34 that convert light photons received on the detector surface during gel and blot imaging to electrical signals that are representative of the number of photons or the intensity of radiation impacting individual pixel regions of the detector surface. Row electrodes 36 and column electrodes 38 are connected to the pixels 34—with each pixel being generally defined at a row and column crossing, at which a row electrode or scan line 36 crosses a column electrode or data line 38. Contact fingers 40 are formed for receiving signals from the column electrodes 38, and contact leads 42 are provided for communicating the signals between the contact fingers 40 and readout electronics (not shown) that convert analog signals generated by the pixels 34 to digital values that can be processed, stored, and displayed following reconstruction of an image.

Figure 4:
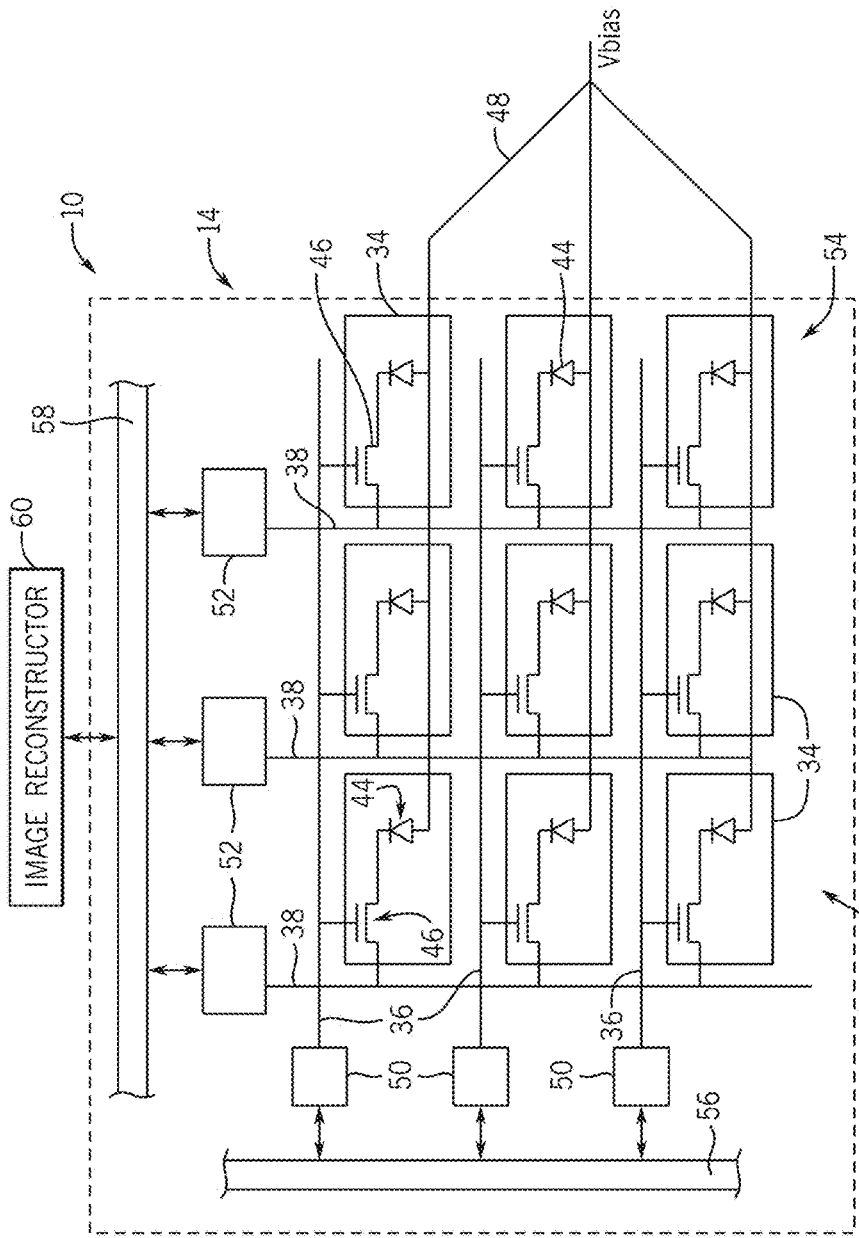
FIG. 4 is a schematic view of an amorphous silicon photodetector array of the flat panel detector of FIG. 1, according to an embodiment of the invention.

As best illustrated in FIG. 4, the array elements or pixel regions 34 are organized in rows and columns 36, 38, with each pixel 34 including a photodiode 44 and associated thin film transistor 46 (TFT). The cathode of each diode 44 is connected to the source of the transistor 46, and the anodes of all diodes 44 are connected to a negative bias voltage 48. The gates of the transistors 46 in each row are connected together and the row electrodes 36 are connected to scanning electronics 50 (i.e., row drivers) described in further detail below. The drains of the transistors 46 in a column are connected together and an electrode of each column 38 is connected to readout electronics 52. In operation, the photodiodes 44 are biased by way of the negative bias voltage 48 and discharged at the appropriate time by way of transistors 46, with the transistors 46 controlling electrical discharge from the appropriate corresponding columns 38. The rows 36 and columns 38 of pixels 34 define an image matrix 54, having a height and width of desired size. For the flat panel detector 14, which is utilized for gel and blot imaging, the image matrix may be constructed to have dimensions of approximately 40×40 cm, with an array of 2048 columns×2048 rows at 200 µm pitch, according to one embodiment. It is recognized, however, that the flat panel detector 14 may be constructed to have different dimensions and a different array size at a different pitch, such as pixels at a 100 µm pitch or 50 µm pitch, for example. In general, the size of the panel is able to accommodate up to four mini gels/membranes or one large gel/membrane, such that flexibility for particular imaging needs or requirements can be easily met.

Each of the rows and columns of pixels 36, 38 is coupled to a row bus 56 and column bus 58, respectively. The row bus 56 includes a plurality of conductors for enabling readout from various columns of the detector, as well as for disabling rows and applying a charge compensation voltage to selected rows, where desired. The column bus 58 includes additional conductors for reading out the columns while the rows are sequentially enabled. The row bus 56 is coupled to a series of row drivers 50, each of which commands enabling of corresponding row 36. Similarly, readout circuitry or electronics 52 is coupled to column bus 58 for reading out all columns 38. According to one embodiment, in response to sequential trigger signals from row drivers 50, all columns are simultaneously read out by readout electronics 52.

As mentioned above, a thin film transistor 46 is provided at each crossing location for each photodiode of each pixel region 34. As each row 36 is enabled by row drivers 50, signals from each photodiode 44 may be accessed via readout circuitry 52, and converted to digital signals for subsequent processing and image reconstruction—such as by way of an image reconstructor 60 provided separately from the flat panel imaging system 10. While image reconstructor 60 is shown separate from flat panel imaging system 10 in FIG. 4, it is recognized that in another embodiment the image reconstructor 60 could be incorporated into the flat panel imaging system 10.

According to embodiments of the invention, the flat panel imaging system 10 generally described in FIGS. 1-4 may be utilized for imaging gel and/or blot samples of macromolecules (DNA, RNA and proteins), with imaging being performed according to one of various detection techniques, including chemiluminescence detection, fluorescent detection, and colorimetric detection. Analysis of standalone gel samples and blot samples (e.g., western blot imaging and southern blot imaging, for example) may be performed using the flat panel imaging system 10.

According to one embodiment, the flat panel imaging system 10 is utilized for chemiluminescence Western blot imaging. Accordingly, as shown in FIG. 1, the lid 18 of the flat panel imaging system 10 is constructed as a "dark lid" that provides for an efficient capture of light emitted from the chemiluminescent reaction in the blot 20 by the flat panel detector 14. The dark lid 18 mates with the base portion 16 such that the outer housing 12 forms a light-tight box within which a digital image acquisition of the chemiluminescence blot imaging can be performed.

Figure 5:
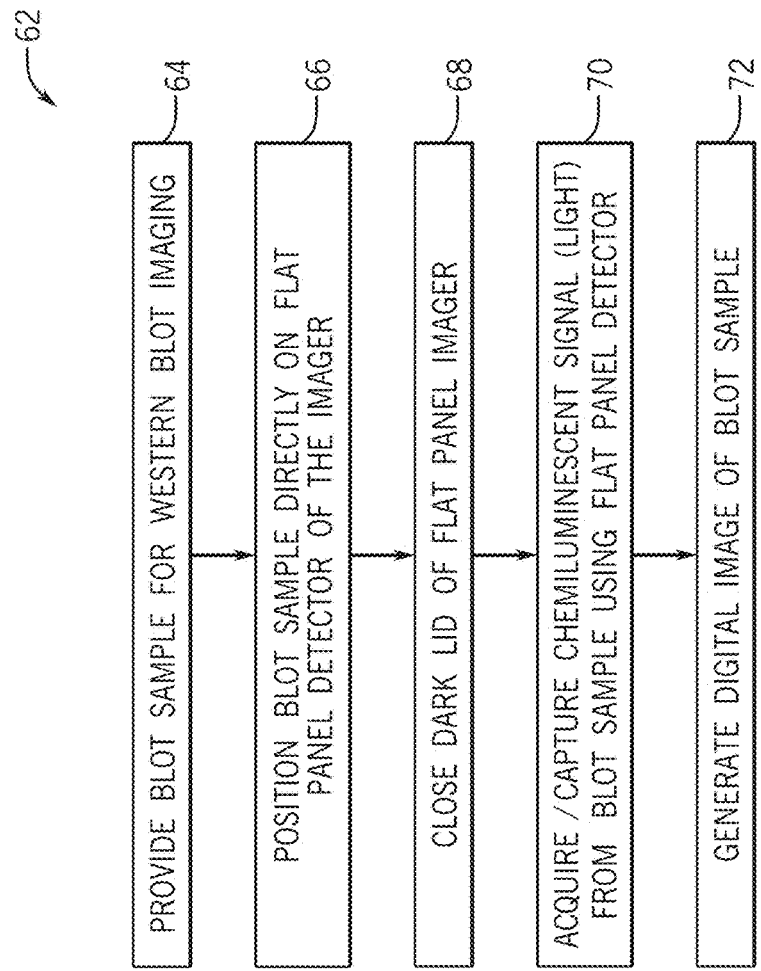
FIG. 5 is a flowchart illustrating a technique for digital image acquisition of a chemiluminescence blot using the flat panel imaging system of FIG. 1, according to an embodiment of the invention.

Referring now to FIG. 5, and with continued reference back to FIGS. 1-4, a technique 62 of image generation for chemiluminescence blot imaging is illustrated according to an embodiment of the invention—with the technique being described for a Western blot technique. The technique 62 begins at STEP 64 with the providing of a blot sample 20 that is prepared in accordance with a manner commonly known in the art. In providing the blot sample 20, proteins of the sample are first separated using gel electrophoresis—with the separation of proteins being by isoelectric point (pI), molecular weight, electric charge, or a combination of these factors, for example. The gel electrophoresis may employ polyacrylamide gels and buffers loaded with sodium dodecyl sulfate (SDS), for example, to maintain polypeptides in a denatured state once they have been treated with strong reducing agents to remove secondary and tertiary structure (e.g., disulfide bonds [S—S] to sulfhydryl groups [SH and SH]) and to allow separation of proteins by their molecular weight. Sampled proteins become covered in the negatively charged SDS and, upon applying of a voltage along the gel, move to the positively charged electrode through the acrylamide mesh of the gel. The proteins travel only in one dimension along the gel for most blots, with proteins migrating through the gel at different speeds (rates of advancement) dependent on their size—with the different rates of advancement (different electrophoretic mobilities) separating the proteins into bands.

In order to make the proteins accessible to antibody detection they are moved from within the gel onto a membrane made of nitrocellulose or polyvinylidene difluoride (PVDF), for example, such as by way of electroblotting—with the proteins maintaining the organization they had within the gel. In performing the antibody detection process, the membrane is "probed" for the protein of interest with a modified antibody which is linked to a reporter enzyme that—when exposed to an appropriate substrate—drives a colorimetric reaction and produces a color. The antibody detection is typically a two-step process. In a first step, a dilute solution of primary antibody (generally between 0.5 and 5 micrograms/mL) is incubated with the membrane under gentle agitation. Typically, the solution is composed of buffered saline solution with a small percentage of detergent, and sometimes with powdered milk or BSA. After rinsing the membrane to remove unbound primary antibody, the membrane is exposed to another antibody (i.e., a secondary antibody) directed at a species-specific portion of the primary antibody. The secondary antibody is usually linked to biotin or to a reporter enzyme such as alkaline phosphatase or horseradish peroxidase (HRP), which means that several secondary antibodies will bind to one primary antibody and enhance the signal.

In order to generate chemiluminescence in the blot sample 20, a substrate molecule is then provided with which the enzyme in the secondary antibody reacts—i.e., the substrate molecule will be converted by the enzyme to a colored reaction product or luminescence that will be visible on the membrane, with the colored reaction product or luminescence being produced in proportion to the amount of protein. As an example, in an embodiment where a HRP is the enzyme in the secondary antibody, a luminol-based substrate is applied to produce a chemiluminescent signal released in the form of light. In the presence of HRP and a peroxide buffer, the luminol oxidizes and forms an excited state product that emits light as it decays to the ground state. A blot sample 20 that generates a chemiluminescent signal released in the form of light is thus provided at STEP 64.

Referring still to FIG. 5, in a next step of technique 62, the blot sample 20 is placed onto the flat panel detector 14 of the imager 10, as indicated at STEP 66. More specifically, the sample 20 is placed on the top protective layer 22 of the flat panel detector 14 such that it is in direct contact therewith. Accordingly, the blot sample 20 is positioned immediately adjacent to the amorphous silicon photodetector array 24 of the flat panel detector 14. Upon placement of the blot sample 20 on the flat panel detector 14, the dark lid 18 of the flat panel imaging system 10 is closed at STEP 68 and acquisition/capture of the chemiluminescent signal (i.e., light) emitted from the blot sample 20 via the flat panel detector 14 is commenced at STEP 70. Light emitted from the blot sample 20 is converted to electric charge and stored in the photodiodes 44 of the photodetector pixels 34. The charge is read out by activating the thin film transistors 46 associated with the photodiodes 44, with the read-out time being adjustable as desired for properly detecting the chemiluminescent light signal emitted from the blot sample 20.

The read-out of the charges stored in the photodiodes 44 is performed by read-out electronics 52 of the flat panel detector 14, which convert the charge to digital signals. The digital signals generated by the read-out electronics 52 may then be provided to an image reconstructor 60 for subsequent processing and generation of a digital image of the western blot sample, as indicated at STEP 72, with the digital image displaying specific proteins in the blot sample so as to allow for further data analysis thereof, such as evaluation of protein levels, molecular weight analysis, and/or another quantitative analysis thereof, for example.

Figure 6:
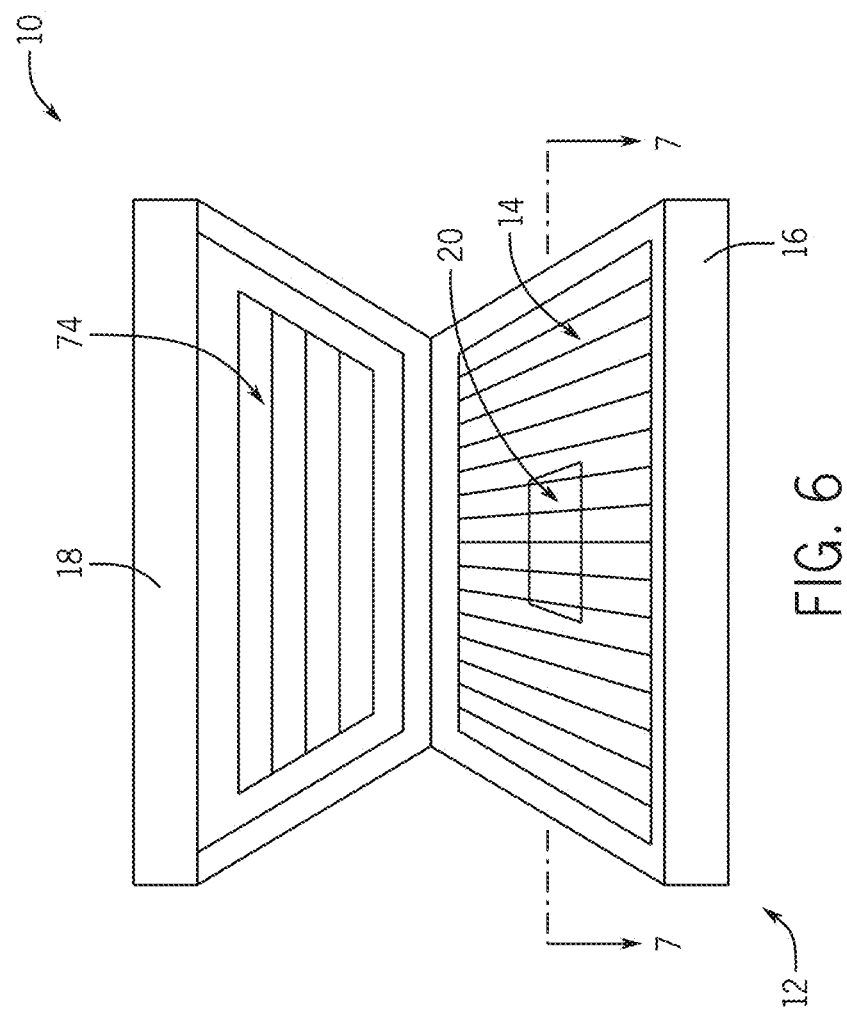
FIG. 6 is an elevated perspective view of a flat panel imaging system, including a flat panel detector, according to an embodiment of the invention.
Figure 7:
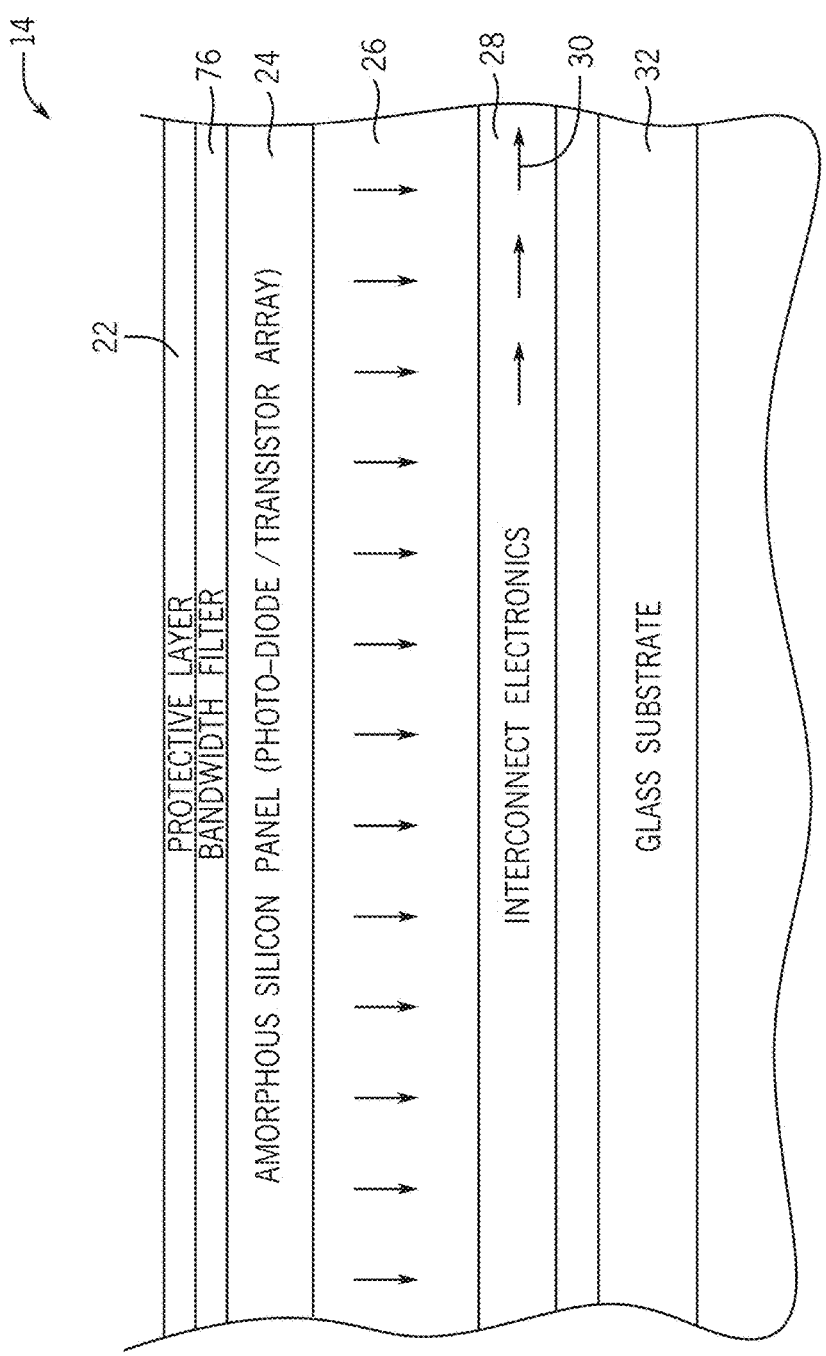
FIG. 7 is an exploded sectional view of the flat panel detector of FIG. 6 taken along line VII-VII, according to an embodiment of the invention.

According to another embodiment, the flat panel imaging system 10 generally described in FIGS. 1-4 is utilized for fluorescence imaging of a gel sample. In such an embodiment, the flat panel imaging system 10 may be modified as shown in FIGS. 6 and 7 in order to accommodate such fluorescence imaging. Referring first to FIG. 6, the flat panel imaging system 10 is shown therein as including a transillumination light source 74 that provides illumination for performing of fluorescence imaging when required. In one embodiment—such as would be used in DNA/RNA sequence detection—the transillumination light source 74 is an ultraviolet (UV) light source that is incorporated into the lid 18 of the housing 12. In another embodiment—such as would be used in protein detection—the light source 74 is a colored light source (e.g., red/green/blue (RGB) light source or blue light source) that is incorporated into the lid 18 of the housing 12. The light source 74 is used in conjunction with a light-activated fluorescent stain or reagent to generate a light emission from the gel or blot sample 20. As shown in FIG. 7, a narrow bandwidth filter 76 may be included in the flat panel imaging system 10, with the filter 76 being incorporated into the flat panel detector 14 to filter the light source emission from light source 74 from the light generated by the gel sample responsive to excitation of the fluorescent reagent by the light source. According to another embodiment, a combination of a long pass filter and short pass filter could be used instead of the narrow bandwidth filter 76.

Figure 8:
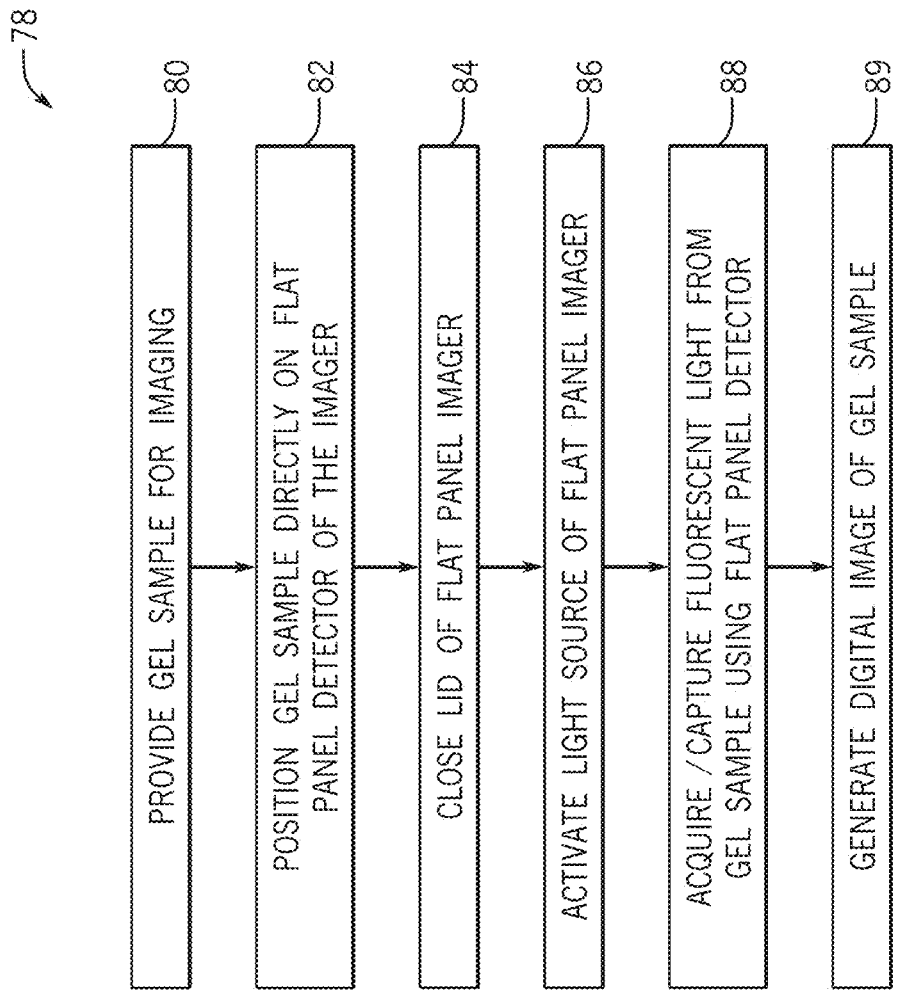
FIG. 8 is a flowchart illustrating a technique for digital image acquisition of a fluorescence blot using the flat panel imaging system of FIG. 6, according to an embodiment of the invention.

Referring now to FIG. 8, and with continued reference back to FIGS. 1-4 and FIGS. 6 and 7, a technique 78 of image generation for fluorescence imaging of a gel sample is illustrated according to an embodiment of the invention. The technique begins 78 at STEP 80 with the providing of a gel sample 20 (i.e., no membrane) that is prepared in accordance with a manner commonly known in the art. The gel sample 20 is solidified to the extent that it can be provided as a standalone sample placed directly onto the flat panel detector 14—with the sample typically having a jello-like consistency. The gel sample 20 may be in the form of a DNA/protein sample in agarose or polyacrylamide gel, with gel electrophoresis being performed to separate proteins/DNA in the sample.

The gel sample 20, and more specifically the macromolecules in the gel sample, are fluorescently labeled to make them visible. A fluorescent reagent is utilized that causes a light to be emitted from the gel sample when the reagent is excited by a light source—such as light source 74 (UV or colored light source). The fluorescent reagent may be any of a number of stained nucleic acid gels that can be excited by a UV or colored light source. In one embodiment, where DNA/RNA is analyzed via excitation with UV light, the reagent may be ethidium bromide (EtBr), iridium bromide, or SYBR® Green, for example. In another embodiment, where protein is analyzed via excitation with colored light (or UV), the reagent may be Texas Red or SYPRO® Ruby, for example. Similar to enzyme reactions (as in chemiluminescence), the fluorescent reagents may be optimized for optimal signal-to-noise ratio, as if the degree of fluorescent labeling is too low, the signal will be weak and if the degree of fluorescent labeling is too high, the signal will also be weak due to the inactivation of the detection reagent or quenching of the signal caused by a phenomenon known as Forster resonance energy transfer (FRET). Thus, upon applying of the fluorescent reagent, a completed fluorescence blot sample 20 is provided at STEP 80.

Referring still to FIG. 8, in a next step of technique 78, the gel sample 20 is placed onto the flat panel detector 14 of the imager 10, as indicated at STEP 82. More specifically, the gel sample 20 is placed on the top protective layer 22 of the flat panel detector 14 such that it is in direct contact therewith. Accordingly, the gel sample 20 is positioned immediately adjacent to the amorphous silicon photodetector array 24 of the flat panel detector 14. Upon placement of the gel sample 20 on the flat panel detector 14, the lid 18 of the flat panel imaging system 10 is closed at STEP 84 and the light source is activated at STEP 86. An output of light from the light source 74 excites the fluorescently labeled sample and causes light to be emitted from the gel sample 20, and this light is acquired/captured by the flat panel detector 14 at STEP 88. The light emitted from the gel sample 20 that is captured by the flat panel detector 14 is converted to electric charge, which is stored in the photodiodes 44 of the photodetector pixels 34 and subsequently read out by activating the thin film transistors 46 associated with the photodiodes 44.

The read-out of the charges stored in the photodiodes 44 is performed by read-out electronics 52 of the flat panel detector 14, which convert the charge to digital signals. The digital signals generated by the read-out electronics 52 may then be provided to an image reconstructor 60 separate from the flat panel detector 14 for subsequent processing and generation of a digital image of the gel sample 20, as indicated at STEP 89. For the technique 78 described above, the digital image generated at STEP 89 will display specific proteins/DNA/RNA in the gel sample so as to allow for further data analysis thereof, such as evaluation of protein levels and quantitative analysis thereof.

Figure 9:
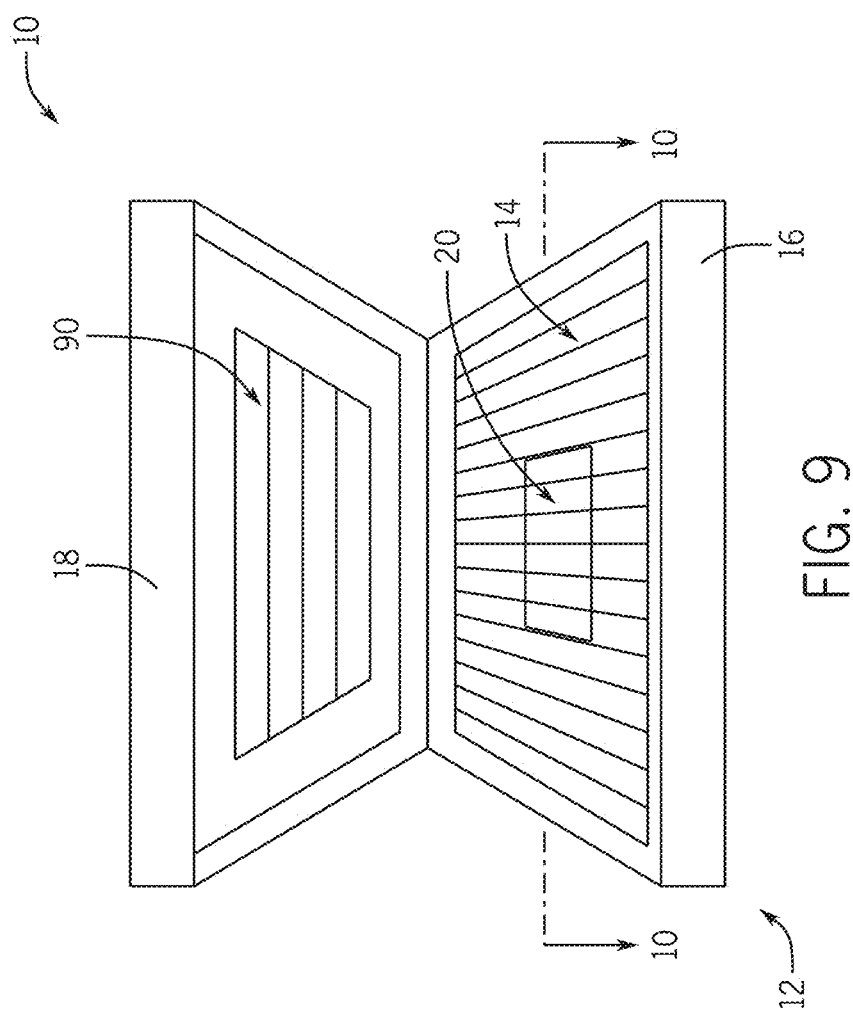
FIG. 9 is an elevated perspective view of a flat panel imaging system, including a flat panel detector, according to an embodiment of the invention.
Figure 10:
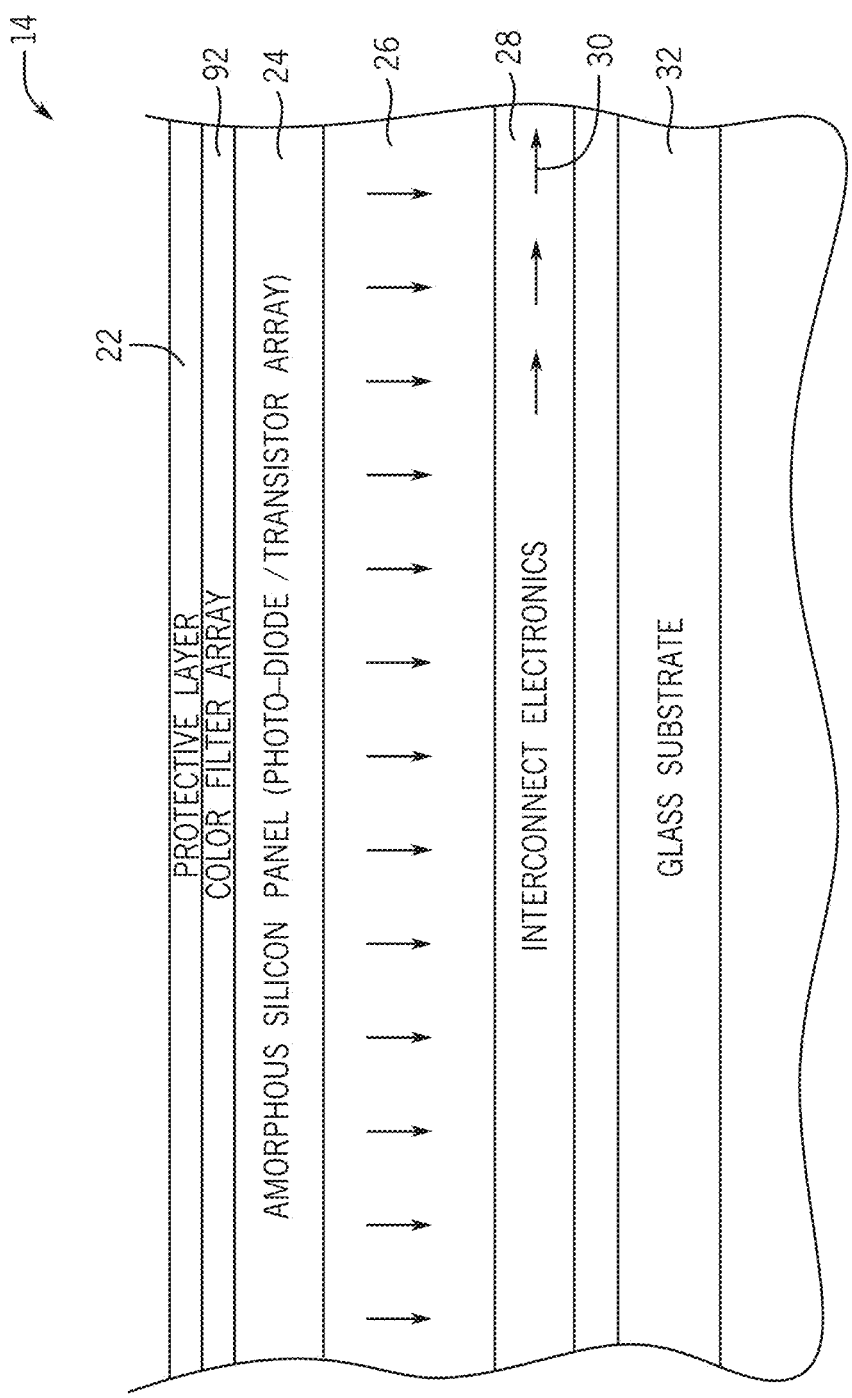
FIG. 10 is an exploded sectional view of the flat panel detector of FIG. 6 taken along line X-X, according to an embodiment of the invention

According to another embodiment, the flat panel imaging system 10 generally described in FIGS. 1-4 is utilized for absorbance or colorimetric (i.e., absorbance) imaging of a gel sample 20. In such an embodiment, the flat panel imaging system 10 may be modified as shown in FIGS. 9 and 10 in order to accommodate such colorimetric imaging. Referring first to FIG. 9, the flat panel imaging system 10 is shown therein as including a transillumination light source 90 to provide illumination for performing of colorimetric imaging. According to one embodiment, the transillumination light source 90 that is incorporated into the lid 18 of the housing 12 is a white light source, and color filter arrays 92 may be placed over the photodetector pixels 34 of the flat panel detector 14 to capture the color information, as is shown in FIG. 10. In another embodiment where the light source 90 is a white light source, each pixel 34 may be divided into three sub-pixels each filtered by a thin-film filter of a specific color—such that each pixel captures all three colors (red/green/blue). In such an embodiment, it is recognized that the displayed image for the gel sample could be a color display that uses the color that has the highest absorbance for the used stain.

While light source 90 is described above as a light source that illuminates the full area of the gel sample, it is understood that in another embodiment the light source 90 could be configured as a source that selectively scans the gel sample using a point, line or patch. By providing a light source that scans the gel sample area using a point, line or patch, the contrast in the colorimetric detection can be increased.

Figure 11:
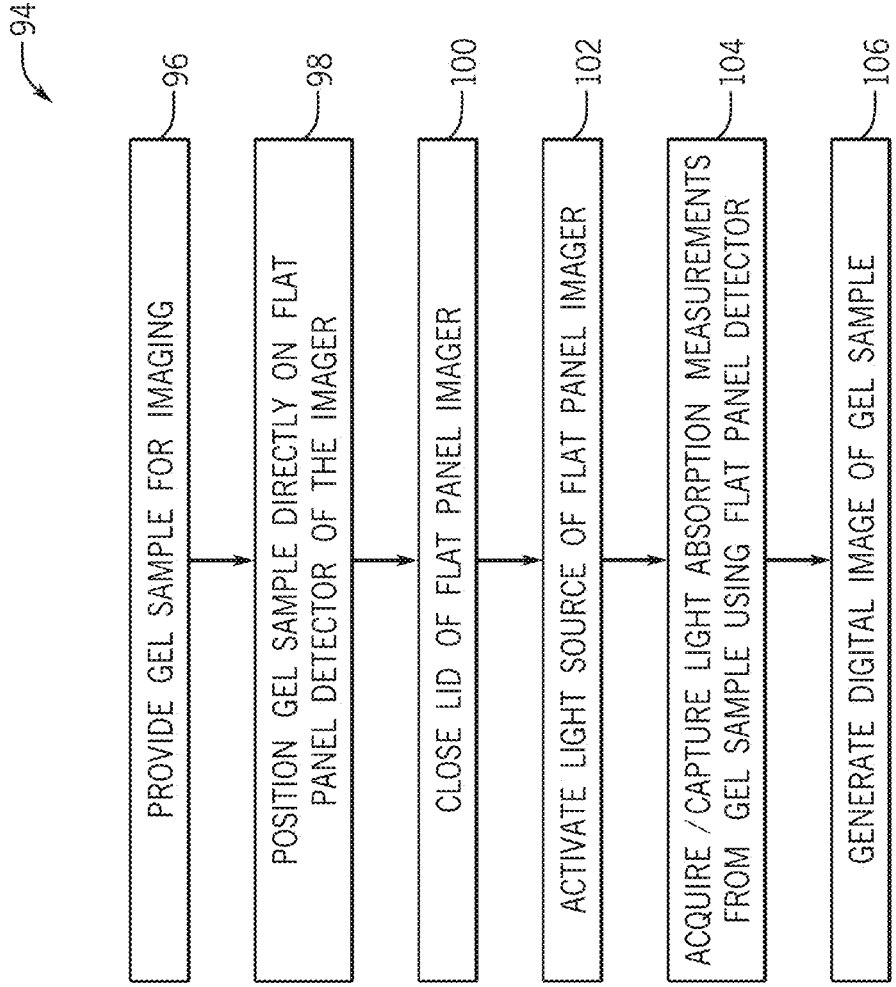
FIG. 11 is a flowchart illustrating a technique for digital image acquisition of a colorimetric blot using the flat panel imaging system of FIG. 9, according to an embodiment of the invention.

Referring now to FIG. 11, and with continued reference back to FIGS. 1-4 and FIGS. 9 and 10, a technique 94 of image generation for colorimetric imaging is illustrated according to an embodiment of the invention. The technique 94 begins at STEP 96 with the providing of a gel sample that is prepared in accordance with a manner commonly known in the art. The gel sample 20 is solidified to the extent that it can be provided as a standalone sample placed directly onto the flat panel detector 14—with the sample typically having a jello-like consistency. As previously set forth in detail above, in providing a sample, proteins are first separated using gel electrophoresis and then exposed to a soluble dye to stain the proteins in the gel sample. Examples of soluble dyes that may be employed to stain the proteins are silver stain and Coomassie stains (e.g., Coomassie® Brilliant Blue dye). Upon a desired staining of the proteins, the gel sample is destained to enable visualization of the proteins, upon completion of which a colorimetric gel sample 20 is provided at STEP 96.

Referring still to FIG. 11, in a next step of technique 94, the gel sample 20 is placed onto the flat panel detector 14 of the imager 10, as indicated at STEP 98. More specifically, the gel sample 20 is placed on the top protective layer 22 of the flat panel detector 14 such that it is in direct contact therewith. Accordingly, the gel sample 20 is positioned immediately adjacent to the amorphous silicon photodetector array 24 of the flat panel detector 14. Upon placement of the gel sample 20 on the flat panel detector 14, the lid 18 of the flat panel imaging system 10 is closed at STEP 100 and the light source 90 is activated at STEP 102. An output of light (white light or colored light) from the light source 90 provides for a densitometry (or absorptiometry) measurement to be taken of the gel sample 20 that measures light absorption through the gel, with the light absorption measurements being acquired/captured by the flat panel detector 14 at STEP 104. The light absorption through the gel sample 20 that is captured by the flat panel detector 14 is converted to electric charge, which is stored in the photodiodes 44 of the photodetector pixels 34 and subsequently read out by activating the thin film transistors 46 associated with the photodiodes 44.

The read-out of the charges stored in the photodiodes 44 is performed by read-out electronics 52 of the flat panel detector 14, which convert the charge to digital signals. The digital signals generated by the read-out electronics 52 may then be provided to an image reconstructor 60 separate from the flat panel detector 14 for subsequent processing and generation of a digital image of the gel sample 20, as indicated at STEP 106. For the technique 94 described above, the digital image generated at STEP 106 will display specific proteins in the gel sample so as to allow for further data analysis thereof, such as evaluation of protein levels and quantitative analysis thereof.

According to additional embodiments of the invention, it is recognized that both the fluorescence imaging technique 78 of FIG. 8 and the colorimetric/absorbance imaging technique 94 of FIG. 11 could be performed on a blot sample rather than a gel sample. That is, macromolecules (protein/DNA/RNA) could be transferred from the gel onto a membrane to create a blot sample that is placed in the flat panel imaging system 10 for image acquisition. In such an embodiment—for colorimetric or chemiluminescence—the member could be wetted such that the blot sample becomes semi-transparent or translucent, allowing light from a light source in the imaging system lid to pass through the sample. While such an embodiment can lead to less exciting light passing through the sample (as compared to the gel sample embodiment) and less light uniformity across the sample/membrane, it is recognized that image acquisition of a blot sample in chemifluorescence imaging and colorimetric/absorbance imaging is recognized to be within the scope of the invention.

EXAMPLES

The following examples were carried out using a flat panel imaging system, such as the flat panel imaging system 10 of FIGS. 1-4. Images of a western blot were acquired via a flat panel imaging system, and these images were compared to images acquired of the same western blot using a CCD-based imaging system and a C-Digit imaging system (LICOR system).

Example 1

In a first example, a sample of 6.25 ng of Actin protein was provided on a western blot—with chemiluminescence detection being used to acquire an image. The Actin protein sample was imaged on each of a flat panel imaging system, a CCD-based imaging system, and a C-Digit imaging system. In performing the image acquisitions with the aforementioned systems, an image of the Actin protein was acquired with the flat panel imaging system using a 12 second acquisition time (i.e., exposure time), an image of the Actin protein was acquired with the CCD system using a 12 minute acquisition time, and an image of the Actin protein was acquired with the C-Digit system using a 12 minute acquisition time. For the acquired images, it was found that a crisper image of the Actin protein was acquired with the flat panel imaging system due to the sensitivity of the flat panel detector and based on the SNR achievable with the flat panel detector.

With respect to the SNRs present in the imaging systems, the SNR is determined for purposes of this example based on a peak signal detected during image acquisition of the Actin protein sample and on a standard deviation of noise across a plurality of pixels in the acquired image (e.g., 100 pixels). The standard deviation of noise, $\sigma_{noise}$, across pixels in the image acquired with the flat panel imaging system is 11, while the $\sigma_{noise}$ across pixels in the image acquired with the CCD system is 35 and the $\sigma_{noise}$ across pixels in the image acquired with the C-Digit system is 30. Based on these standard deviations of noise and the peak signals detected with the respective systems, the SNRs achieved with the respective systems are 305 (+/−10) for the flat panel imaging system, 132 (+/−10) for the CCD system, and 34 (+/−5) for the C-Digit system. Thus, it can be seen that an improved SNR is achievable with the flat panel imaging system, leading to improved resolution and crispness in the images of the Actin protein acquired therewith.

Example 2

Figure 12:
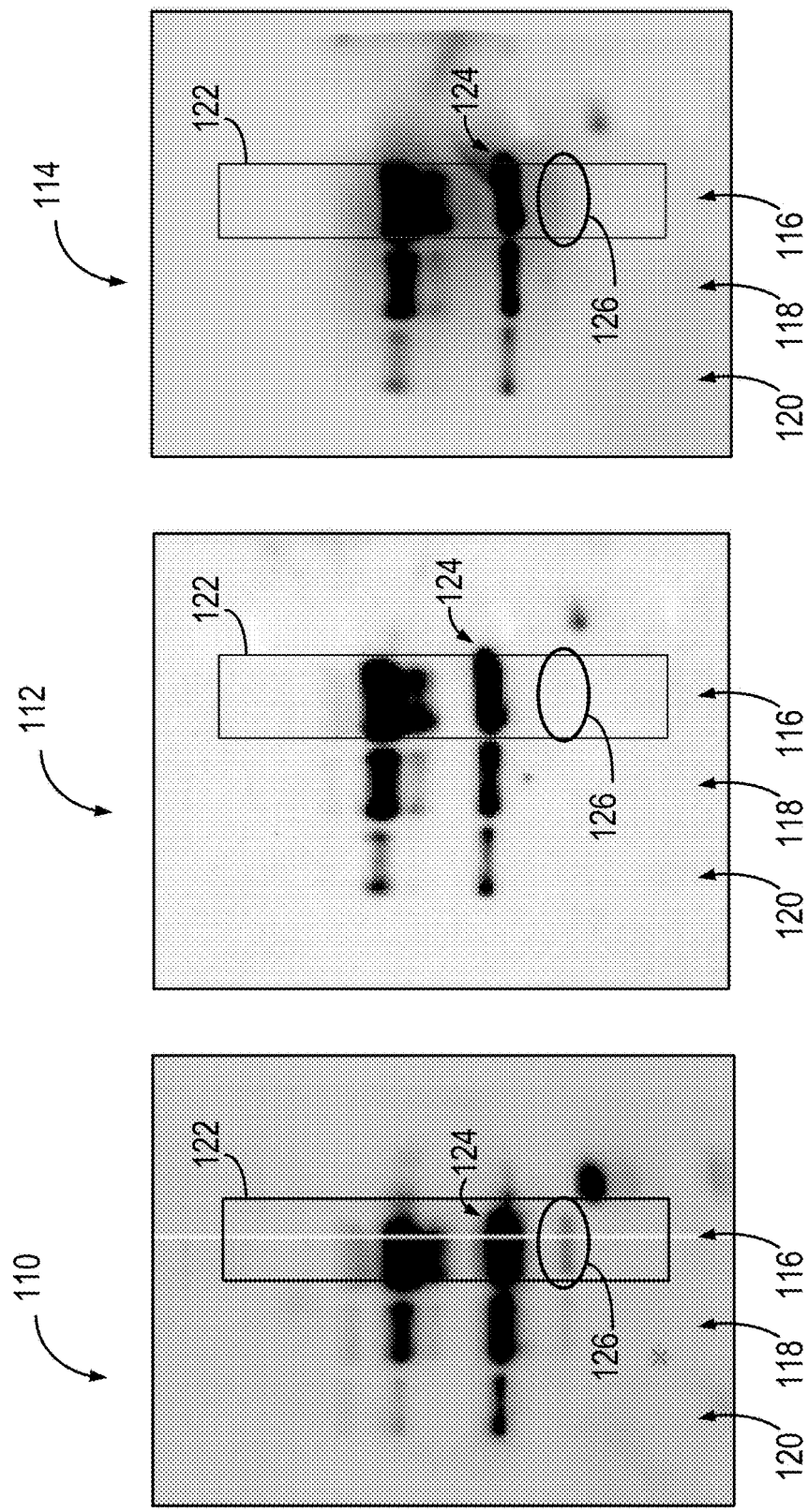
FIG. 12 illustrates images acquired of a cell lysate sample using each of a flat panel imaging system, CCD-based imaging system, and a C-Digit imaging system.

In a second example, a cell lysate sample of unknown makeup was provided on a western blot, with a sample of Actin protein also provided on the western blot to serve as a standard or reference point—with chemiluminescence detection being used to acquire an image. Referring now to FIG. 12, images acquired of the cell lysate western blot are shown therein, with an image 110 of the western blot acquired via use of a flat panel imaging system illustrated in comparison to similar images acquired via the use of a CCD-based imaging system and a C-Digit imaging system, indicated as 112 and 114 respectively. Each of the images 110, 112, 114 includes three lanes therein that are generally referred to as a high concentration lane 116, a medium concentration lane 118, and a low concentration lane 120, in which the concentration of the cell lysate sample is varied.

For performing an image capture of the cell lysate sample, a line scan acquisition is performed. As can be seen in FIG. 12, a line scan—indicated as 122—is performed on the high concentration lane 116 to provide a high quality image thereon. As can be seen in image 110, the flat panel imaging system provides increased sensitivity to light generated by the sample along with improved SNR, such that the image 110 includes increased focus and contrast of the cell lysate lanes 116, 118, 120 shown in the image. With particular respect to high concentration lane 116, it can be seen that the standard/reference Actin protein is visible, as indicated at 124, and that another protein in the sample, indicated at 126, is clearly discernible in the lane 116 of image 110. However, in each of the CCD image 112 and the C-Digit image 114, the protein 126 is not discernible/detectable and. Furthermore, particularly with respect to the C-Digit image 114, it is seen that "bleeding" is present in the image between proteins, based on a large amount of background noise present in the system.

In performing the image acquisitions with the aforementioned systems, an image of the cell lysate sample was acquired with the flat panel imaging system using a 8 second acquisition time (i.e., exposure time), an image of the cell lysate sample was acquired with the CCD system using a 12 minute acquisition time, and an image of the cell lysate sample was acquired with the C-Digit system using a 12 minute acquisition time. As a standard chemiluminescence reaction on a western blot has a lifetime of 10-20 minutes, it is thus recognized that only one or two separate exposures and accompanying image acquisitions might be performed with the CCD system and the C-Digit system, thereby limiting the variations of exposure time that might be desired by an operator and the number of separate images that might be acquired—which may lead to an oversaturated or undersaturated image. Conversely, based on the relatively short exposure time associated with the image acquisition of the flat panel imaging system, the system is recognized as having essentially an infinite dynamic range, as a much larger number of separate exposures and accompanying image acquisitions can be performed during the lifetime of the chemiluminescence reaction, such that an ideal exposure time can be identified for optimum image acquisition. The collection of numerous images via the fast acquisition rate also allows for a decrease in the noise of the acquired images.

Beneficially, embodiments of the invention thus provide a flat panel imaging system 10 having a flat panel detector 14 that functions as a matrix-based light sensor array, with the flat panel detector 14 being composed of an array of pixels each comprising a photodiode-transistor pair that detect/capture light emitted from a gel or blot imaging process that utilizes a chemiluminescence, fluorescence or colorimetric detection technique. Each pixel may be sized so as to provide for reasonable spatial resolution in capturing light from the gel/blot imaging, with pixels down to a size of 50 microns being included in the flat panel detector. The flat panel imaging system provides demanding performance in terms of sensitivity, dynamic range, exposure time, and quantum efficiency, and collects photons directly and efficiently from the gel/blot sample, which eliminates costly high-efficiency imaging optics used with small cooled CCD image sensors and greatly improves the workflow associated with traditional film—with image capture times of less than 10 seconds (e.g., 6 seconds) being achievable. The increase in sensitivity also allows for dramatically decreasing the amount of sample needed, thus reducing anti-body, reagents required, and laboratory animals, saving costs and time, while the fast acquisition speed enables the use of software to obtain virtually infinite dynamic range, reducing time and effort for each experiment. Of still further benefit, the flat panel imaging system also can provide a quasi-stationary image with reasonable signal-to-noise ratio, which is superior to a scan method. The flat panel imaging system also offers compactness for portability.

Therefore, according to one embodiment, a method for generating a digital image in fluorescence detection gel imaging includes providing a gel sample having a gel and a sample of macromolecules therein and placing the gel sample on a flat panel detector of a flat panel imaging system, the flat panel detector comprising an array of photodiodes and transistors that collect light generated from the gel sample. The method also includes illuminating the gel sample using a light source integrated into the flat panel imaging system and collecting light emitted by the gel sample responsive to an excitation of the gel sample by light provided by the light source, with the light emitted by the gel sample being collected by the array of photodiodes of the flat panel detector and converted to electric charges to generate light data. The method further includes processing the light data to generate a digital image of the gel sample, the processing and image generation being performed by an image reconstructor separate from or incorporated into the flat panel imaging system.

According to another embodiment, a method of generating a digital image in fluorescence detection gel imaging includes providing a gel sample labeled with a fluorescent reagent, the gel sample having macromolecules labeled by the fluorescent reagent. The method also includes positioning the gel sample within a flat panel imaging system to provide for capturing of a digital image of the gel sample, the positioning of the gel sample within the flat panel imaging system further including placing the gel sample on a flat panel matrix-based light sensor comprising an array of photodiodes and transistors and closing a lid of the flat panel imaging system to create a closed environment for capturing of the digital image. The method further includes illuminating the gel sample using a light source integrated into the lid of the flat panel imaging system so as to excite the fluorescent reagent causing the gel sample to generate fluorescent light and detecting the fluorescent light emitted by the gel sample using the flat panel matrix-based light sensor, with the fluorescent light being collected by the array of photodiodes, converted to electric charges, and subsequently converted to digital signals. The method still further includes providing the digital signals to an image reconstructor to process the digital signals and generate a digital image of the gel sample.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A flat panel imaging system comprising:
 a housing including a base portion and a lid that collectively form a closed environment to exclude external sources of light from entering the housing; and
 a flat panel detector encased in the base portion, the flat panel detector comprising:
   an array of pixels each pixel comprising a photodiode and a transistor, wherein the photodiode and the transistor of each pixel are configured to convert photons received thereby to electrical signals that are representative of the photons impacting the individual respective pixel;
   a transparent protective layer positioned over the array of pixels to provide protection thereto and provide for transmission of photons therethrough to the array of pixels,
 wherein the protective layer comprises a base layer and a removable top layer, the removable top layer comprising a replaceable layer that may be replaced upon completion of an image acquisition of a gel sample or a blot sample.
2. The flat panel imaging system of claim 1 wherein the protective layer has a thickness of 25-75 micrometers.

3. The flat panel imaging system of claim 1 wherein the protective layer comprises glass, or a plastic material, or a combination of glass and the plastic material.

4. The flat panel imaging system of claim 3 wherein the glass, or the plastic material, or the combination of glass and the plastic material provides a scratch resistant, chemically resistant top surface of the protective layer.

5. The flat panel imaging system of claim 1 wherein the protective layer comprises an angle discriminating film to increase contrast and decrease crosstalk of photons received by the array of pixels.

6. The flat panel imaging system of claim 1 wherein the protective layer comprises a layer of indium tin oxide or a conductive layer configured to protect the array of pixels from artifacts or damage resulting from placement of a statically charged sample on the flat panel detector.

7. The flat panel imaging system of claim 1 wherein photons received by the array of pixels comprise photons generated by, or transmitted through the gel sample or the blot sample placed on the protective layer.

8. The flat panel imaging system of claim 7 wherein the photons generated by or transmitted through the gel sample or the blot sample result from one of a chemiluminescence, a fluorescence, or a colorimetric imaging technique performed on the gel sample or the blot sample.

9. The flat panel imaging system of claim 1 wherein the protective layer provides thermal isolation between the array of pixels and the gel sample or the blot sample placed thereon.

10. The flat panel imaging system of claim 1, further comprising a light source integrated into the flat panel imaging system, the light source illuminating the gel sample or the blot sample.

11. The flat panel imaging system of claim 1 wherein the flat panel detector is sized to accommodate placement of a plurality of gel samples or blot samples thereon for gel and blot imaging.

12. The flat panel imaging system of claim 1 wherein the transistor comprises an active layer formed from an amorphous silicon panel.

13. A flat panel imaging system for generating a digital image in gel and blot imaging, the flat panel imaging system comprising:
    a housing comprising a base portion and a lid, the base portion and the lid collectively form a closed environment to exclude external sources of light from entering the housing;
    a flat panel detector encased in the base portion to collect image data from a gel sample or a blot sample, the flat panel detector comprising:
        a matrix-based light sensor that receives light generated by or transmitted through the gel sample or the blot sample being imaged, the matrix-based light sensor comprising an array of photodiodes and transistors configured to convert light received thereby to electrical signals that are representative of the light; and
        a transparent protective layer positioned over the matrix-based light sensor and on which the gel sample or the blot sample is positioned thereon, the transparent protective layer constructed to provide for transmission of the light therethrough while not degrading a modulation transfer function (MTF) of the matrix-based light sensor,
    wherein the protective layer comprises a base layer and a removable top layer, the removable top layer comprising a replaceable layer that may be replaced upon completion of an image acquisition of the gel sample or the blot sample.

14. The flat panel imaging system of claim 13 wherein the protective layer provides thermal isolation between the matrix-based light sensor and the gel sample or the blot sample.

15. The flat panel imaging system of claim 13 wherein the protective layer comprises glass, or a plastic material, or a combination of glass and the plastic material.

16. The flat panel imaging system of claim 13 wherein the flat panel detector is sized to accommodate placement of a plurality of gel samples or blot samples thereon for gel and blot imaging.

17. A flat panel detector for generating a digital image of a gel sample or a blot sample, the flat panel detector comprising:
    a two-dimensional array of pixels each pixel comprising a photodiode and a transistor, wherein the photodiodes are configured to convert light generated by or transmitted through the gel sample or the blot sample to electrical signals that are representative of the light and the transistors are configured to store the electrical signals for read-out by detector electronics, wherein the two-dimensional array of pixels comprises amorphous silicon, an amorphous metal oxide, or organic semiconductors; and
    a protective layer positioned over the two-dimensional array of pixels and on which the gel sample or the blot sample is positioned thereon, the protective layer comprising an optically transparent layer that provides for transmission of the light therethrough while providing protection to the two-dimensional array of pixels,
    wherein the protective layer comprises a base layer and a removable top layer, the removable top layer comprising a replaceable layer that may be replaced upon completion of an image acquisition of the gel sample or the blot sample.

18. The flat panel detector of claim 17 wherein the protective layer provides thermal isolation between the array of pixels and the gel sample or the blot sample.

19. The flat panel detector of claim 17 wherein the array of pixels is sized to accommodate placement of a plurality of gel samples or blot samples thereon for gel and blot imaging.

* * * * *